United States Patent
Diolaiti

(10) Patent No.: US 11,859,967 B2
(45) Date of Patent: Jan. 2, 2024

(54) SYSTEMS AND METHODS FOR SENSOR BASELINE ADJUSTMENT

(71) Applicant: Intuitive Surgical Operations, Inc., Sunnyvale, CA (US)

(72) Inventor: Nicola Diolaiti, Menlo Park, CA (US)

(73) Assignee: INTUITIVE SURICAL OPERATIONS, INC., Sunnyvale, CA (US)

(*) Notice: Subject to any disclaimer, the term of this patent is extended or adjusted under 35 U.S.C. 154(b) by 78 days.

(21) Appl. No.: 17/470,380

(22) Filed: Sep. 9, 2021

(65) Prior Publication Data
US 2022/0082378 A1 Mar. 17, 2022

Related U.S. Application Data

(60) Provisional application No. 63/077,275, filed on Sep. 11, 2020.

(51) Int. Cl.
| | |
|---|---|
| *G01B 21/20* | (2006.01) |
| *A61B 34/20* | (2016.01) |
| *A61B 34/35* | (2016.01) |

(52) U.S. Cl.
CPC .............. *G01B 21/20* (2013.01); *A61B 34/20* (2016.02); *A61B 34/35* (2016.02)

(58) Field of Classification Search
None
See application file for complete search history.

(56) References Cited

FOREIGN PATENT DOCUMENTS

| WO | WO-2020014201 A1 | 1/2020 |
|---|---|---|
| WO | WO-2020014207 A1 | 1/2020 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Alvaro E Fortich
*Assistant Examiner* — Carl F. R. Tchatchouang
(74) *Attorney, Agent, or Firm* — Haynes & Boone, LLP.

(57) ABSTRACT

A tool recognition system may comprise a tool recognition assembly and a control system in communication with the tool recognition assembly. The control system may comprise a processor and a memory comprising machine-readable instructions. When executed by the processor, the instructions may cause the control system to receive a first baseline sensor value from the tool recognition assembly and determine a baseline adjustment threshold based on the first baseline sensor value. The instructions may also cause the control system to receive first monitored sensor data from the tool recognition assembly and compare the first monitored sensor data to the baseline adjustment threshold for a predetermined duration. If the comparison satisfies a comparison criterion, a second baseline sensor value may be established using the first monitored sensor data.

20 Claims, 10 Drawing Sheets

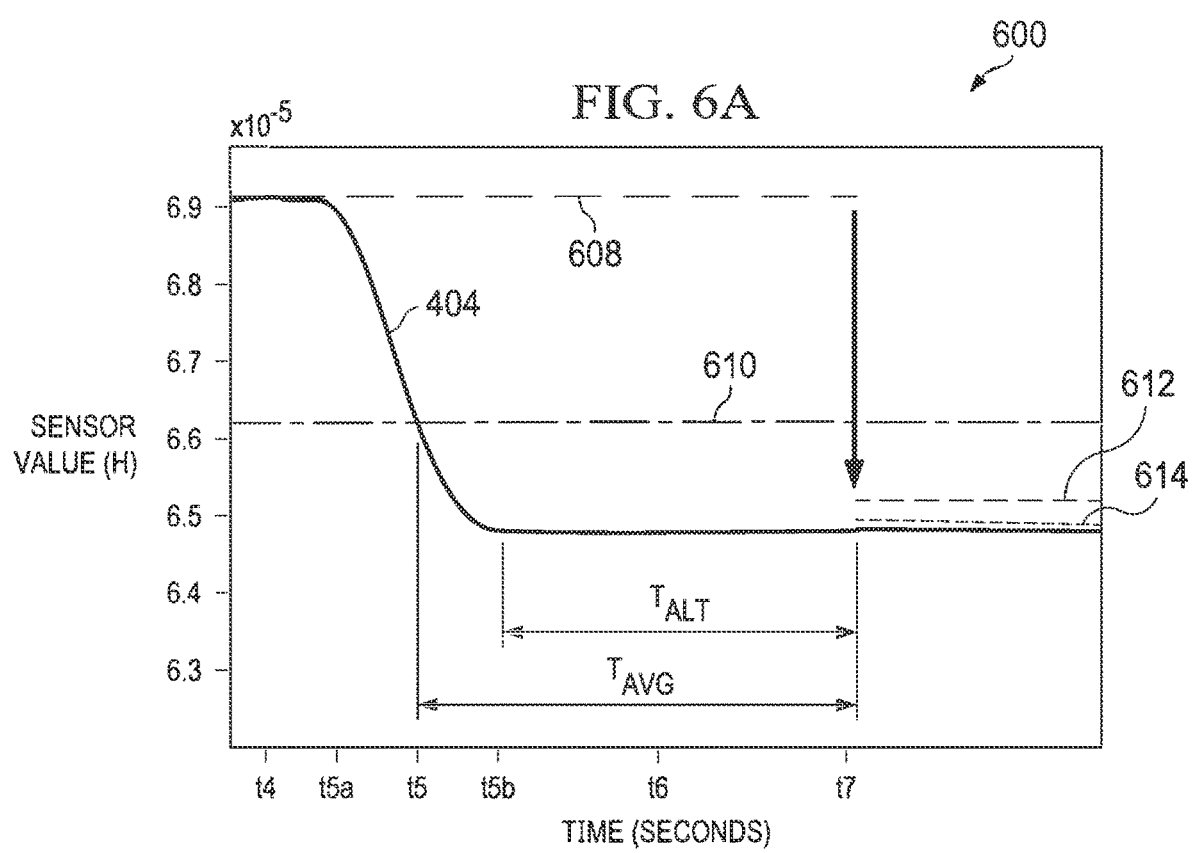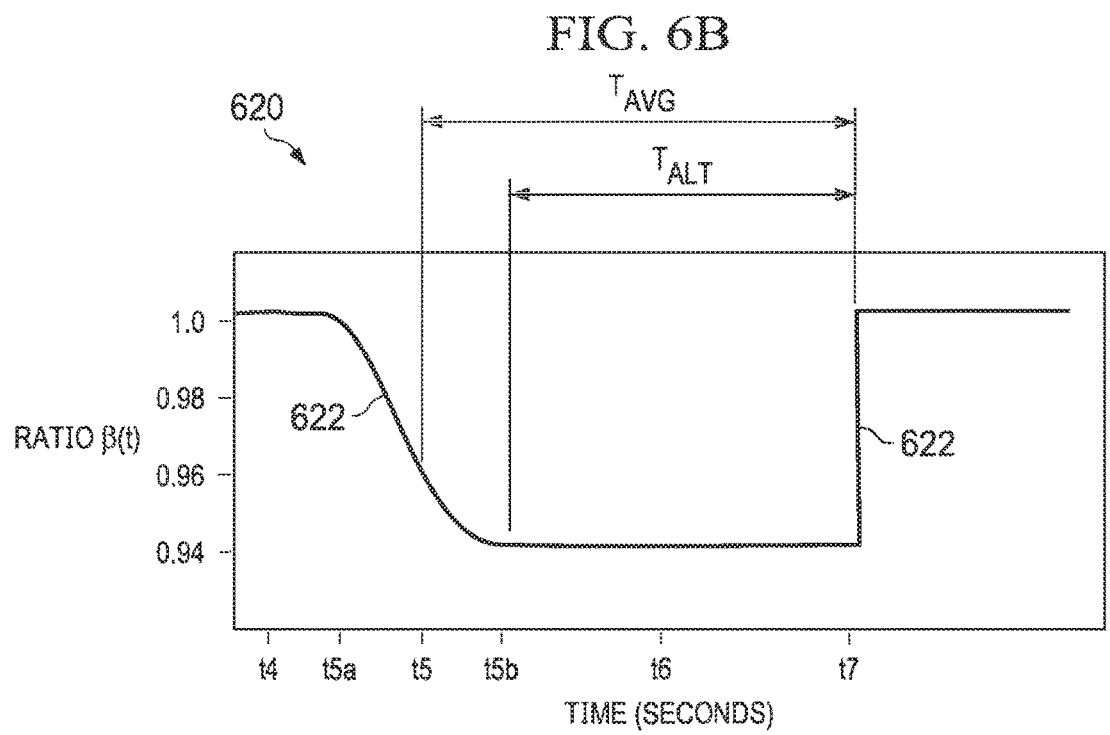

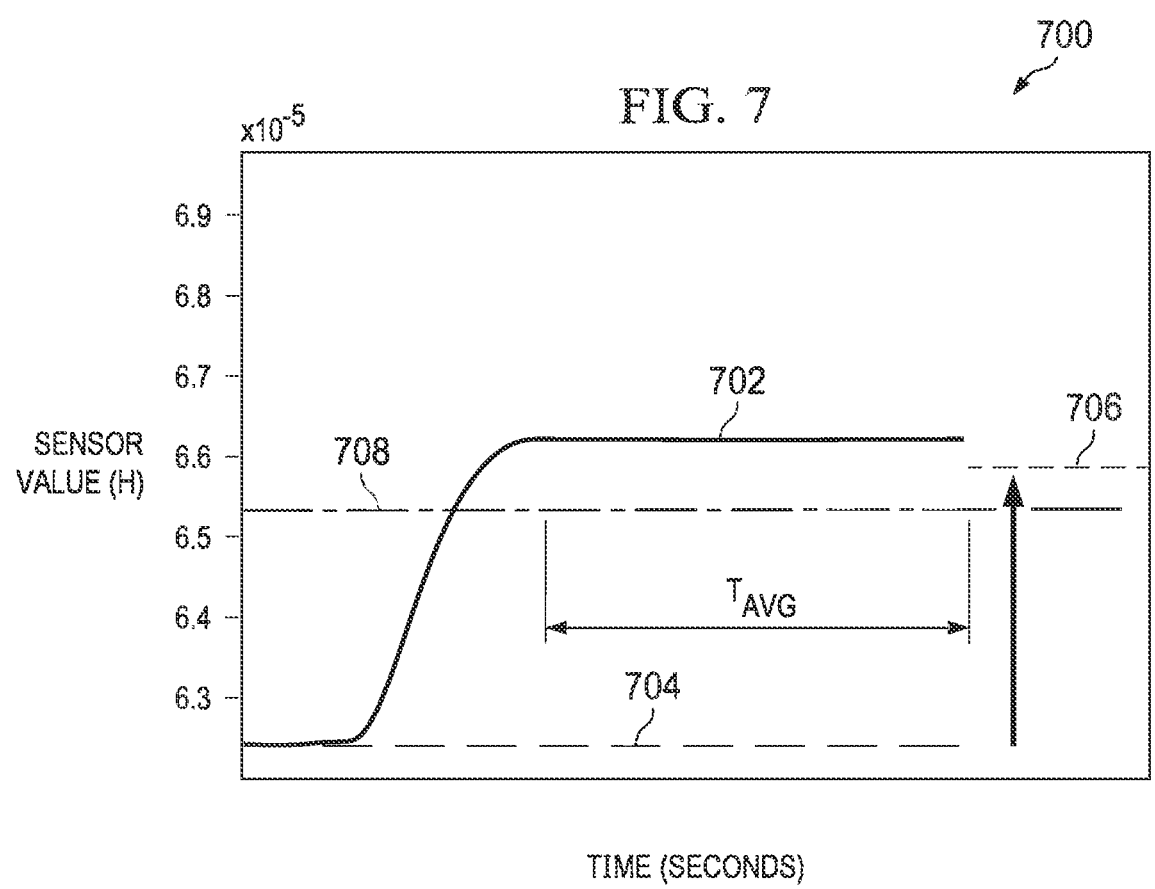

SYSTEMS AND METHODS FOR SENSOR BASELINE ADJUSTMENT

CROSS-REFERENCE TO RELATED APPLICATIONS

This application claims priority to and the benefit of U.S. Provisional Application 63/077,275 filed Sep. 11, 2020, which is incorporated by reference herein in its entirety.

FIELD

Examples described herein are related to systems and methods for detecting an error with a baseline sensor value used to determine a tool installation and adjusting the baseline sensor value with minimal workflow disruption.

BACKGROUND

Minimally invasive medical techniques may generally be intended to reduce the amount of tissue that is damaged during medical procedures, thereby reducing patient recovery time, discomfort, and harmful side effects. Some minimally invasive medical tools may be teleoperated or otherwise robot or computer assisted. Proper installation and recognition of medical instruments to robot-assisted medical systems allows for safe and effective use of the instruments during medical procedures. Accordingly, systems and methods to determine proper installation, allow for quick correction of installation errors, and enable recognition of medical instruments may promote efficient and safe medical procedures.

SUMMARY

The following presents a simplified summary of various examples described herein and is not intended to identify key or critical elements or to delineate the scope of the claims.

A tool recognition system may comprise a tool recognition assembly and a control system in communication with the tool recognition assembly. The control system may comprise a processor and a memory comprising machine-readable instructions. When executed by the processor, the instructions may cause the control system to receive a first baseline sensor value from the tool recognition assembly and determine a baseline adjustment threshold based on the first baseline sensor value. The instructions may also cause the control system to receive first monitored sensor data from the tool recognition assembly and compare the first monitored sensor data to the baseline adjustment threshold for a predetermined duration. If the comparison satisfies a comparison criterion, a second baseline sensor value is established using the first monitored sensor data.

A method may comprise receiving a first baseline sensor value from a tool recognition assembly and determining a baseline adjustment threshold based on the first baseline sensor value. The method may also comprises receiving first monitored sensor data from the tool recognition assembly and comparing the first monitored sensor data to the baseline adjustment threshold for a predetermined duration. If the comparison satisfies a comparison criterion, a second baseline sensor value may be established using the first monitored sensor data.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 6A illustrates a graph of measured sensor values of a target reader during a downward baseline adjustment, according to some examples.

FIG. 6B illustrates a graph of the ratio of the measured sensor value to the baseline sensor value over a period during which the downward adjustment of the baseline value occurs, according to some examples.

FIG. 7 illustrates a graph of measured sensor values of a target reader during an upward baseline adjustment, according to some examples.

Figure 1A:
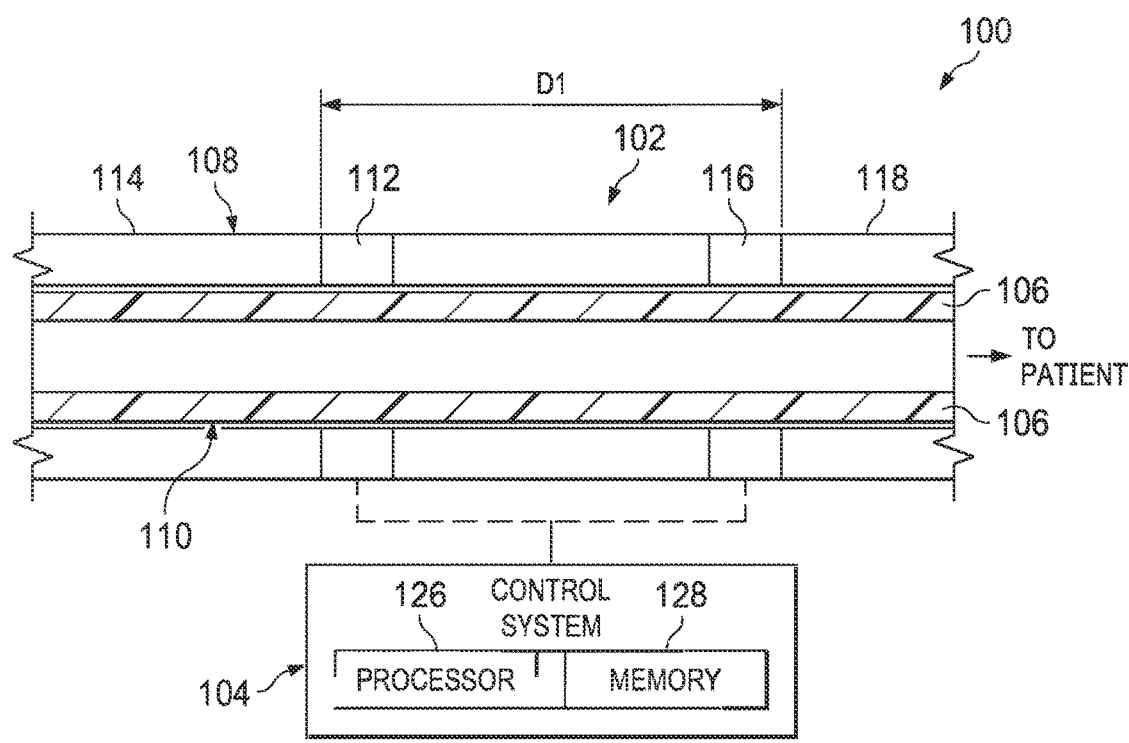
FIGS. 1A-1E illustrate a tool recognition system for recognizing the insertion of a tool according to some examples.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

To safely and effectively operate a medical instrument system, medical tools may need to be properly installed, positioned, identified, authenticated and/or otherwise received and recognized when mounted to a medical system such as a robot-assisted medical system. Systems and methods for detecting tool presence and identity have been described in International Publication No. WO 2020/014201 filed Jul. 9, 2019, which is incorporated by reference herein in its entirety. The technology described herein may provide error detection and correction for a baseline sensor value used to determine a tool installation.

FIG. 1A illustrates a tool recognition system 100 that includes a tool recognition assembly 102 (shown in a cross-sectional view) and a control system 104. In various embodiments, the control system 104 may be a component of the tool recognition assembly 102 and/or a component of a robot-assisted manipulator assembly. The tool recognition assembly 102 may include a mounting member 108 through which a passage 110 extends. A receiving member 106 such as a catheter or other cannulated device may extend through the passage 110 and into a passageway in a patient anatomy. A proximal target reader 112 is mounted near a proximal portion 114 of the mounting member 108, and a distal target reader 116 is mounted near a distal portion 118 of the mounting member 108. The mounting member 108 may be formed of a plastic, a ceramic, or another type of material that minimizes interference with the target readers 112, 116. The ends of the target readers 112, 116 are separated by a distance D1. The target readers 112, 116 may comprise an inductive sensor (e.g., an inductor or inductive coil that detects a change in inductance caused by ferromagnetic and conductive properties of a material), a capacitive sensor, a Hall effect sensor, a photogate sensor, an optical sensor, a magnetic switch, a barcode scanner, a radio frequency identification (RFID) scanner, a relative position sensor, or combinations thereof that are capable of reading corresponding one or more targets on a tool to be inserted into the receiving member 106. Any combination of different types of target readers may be implemented in the tool recognition assembly 102. In some examples, a tool recognition assembly 102 may include a single target reader or three or more target readers. In some examples, target readers with inductive sensors may detect instantaneous inductance values.

The target readers 112, 116 may be in communication with the control system 104 to process data from the target readers (e.g., changes in inductance readings, changes in a magnetic field, changes in intensity of light, changes in colors of light, etc.). The control system may include at least one processor 126 and at least one memory 128. The control system may receive the data from the target readers 112, 116 periodically at regular or irregular intervals or continuously. For example, the target readers 112, 116 may communicate the data to the control system responsive to a change in the data sensed by the target readers (e.g., changes in inductance, changes in resistance, changes in capacitance, changes in a magnetic field, changes in intensity of light, changes in colors of light, etc.) In another example, the data from the target readers are regularly communicated to the control system, either periodically or continuously, and the control system is tasked with determining when the data has changed.

Figure 1B:
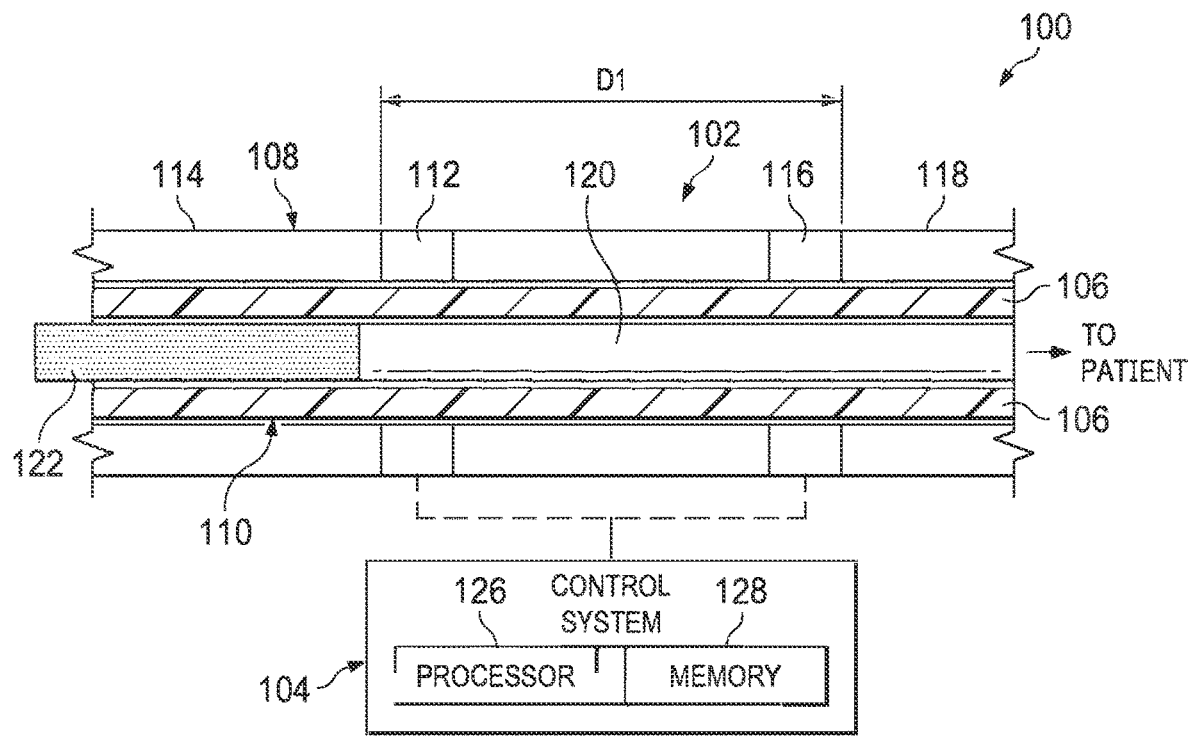
Figure 1C:
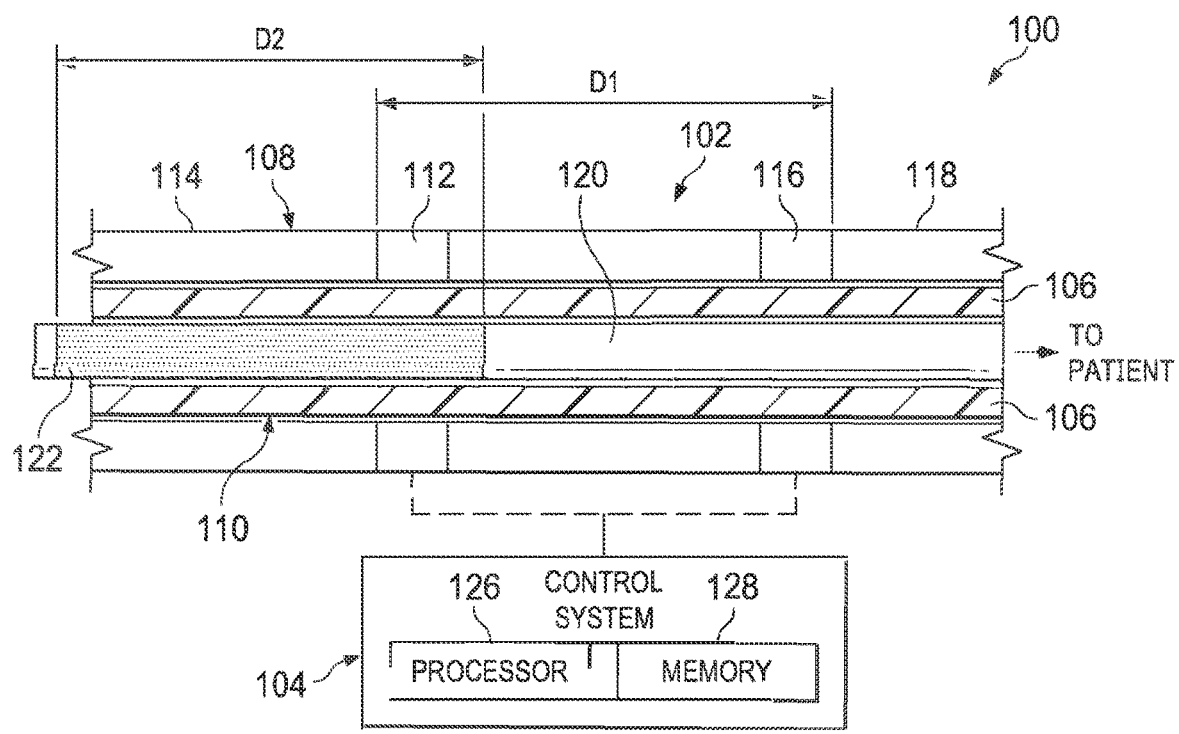

FIG. 1B illustrates the tool recognition system 100 with an elongate tool 120 extending into the receiving member 106. The tool 120 includes a target 122 having a length D2 (FIG. 1C). In this example, the length D2 may be shorter than the length D1 but may be sufficiently long that the target 122 may concurrently extend within both target readers 112, 116. The tool 120 is sized for insertion through the passage 110 and the receiving member 106. As described in greater detail below, the presence and absence of the target 122 may be sensed, detected, or otherwise recognized by the target readers 112, 116. For example, the targets may comprise a ferromagnetic material (e.g., a metal cylinder, a metallic coating), one or more apertures, a surface or material with varied optical absorption characteristics, a barcode, an RFID chip, or combinations thereof that may be sensed, detected, or otherwise recognized by a target reader. In one example, a target reader may detect the presence of a target by detecting an inductance and/or a change in inductance when the target is placed in proximity to a target reader. In some examples, the tool may include a single target 122, but in other examples may include two or more target readers. There may be a different number of targets than there are target readers. The tool 120 may be any of a variety of tools including an imaging tool (e.g. a vision probe), an investigation tool (e.g., a biopsy probe), or a treatment tool (e.g. an ablation probe).

The tool recognition assembly 102 may be configured to detect if the tool 120 is fully inserted into the receiving member 106. The tool 120 may be considered fully inserted, for example, when the tool 120 is inserted to such a degree as to permit the tool 120 being used within the body of a patient; inserted to such a degree that a distal end of the tool 120 is at, or within a predetermined distance of, a distal end of the receiving member 106; inserted to such a degree that the tool 120 extends to a proximal end of the receiving member 106; inserted to such a degree that the tool 120 extends through the mounting member 108; inserted to such a degree that a distal portion of the tool 120 extends a predetermined distance past a distal end of the receiving member; or combinations thereof.

FIG. 1A, may illustrate a configuration of the tool recognition assembly 102 and the receiving member 106 after a set-up process in which the tool recognition assembly 102 and the receiving member 106 are mounted to a platform such as a robot-assisted manipulator assembly. In this configuration, the tool recognition assembly may initiate a latching process in which a baseline value for each of the target readers 112, 116 is registered. If, for example, the target readers include inductance sensors, the baseline value for each of the target readers may be a baseline inductance value corresponding to the inductance value when the passage 110 through the target readers is occupied by the receiving member 106 but unoccupied by the target 122, the tool 120, or other foreign objects. Thus, in this example, the baseline value for each of the target readers may correspond to the inductance value when the receiving member 106 extends through the target readers 112, 116, but the receiving member 106 is empty, with no tools, instruments, or other objects yet inserted through in the receiving member.

Figure 2A:
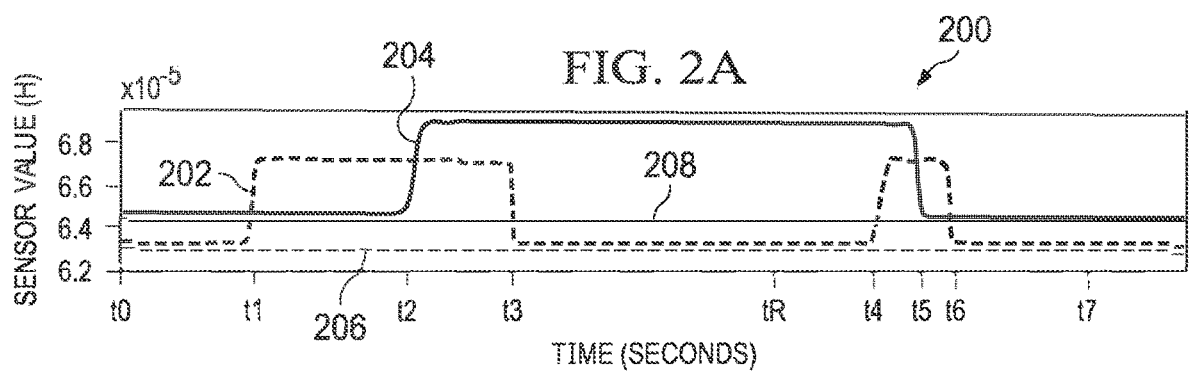
FIG. 2A illustrates a graph of measured sensor values of a set of target readers of a tool recognition system according to some examples.

FIG. 2A illustrates a graph 200 of the measured sensor values of the target readers 112, 116 over time. The graph 200 illustrates the sensor data 202 from the proximal target reader 112 and sensor data 204 from the distal target reader 116. A baseline value 206 is latched or registered for the proximal target reader 112, and a baseline value 208 is latched or registered for the distal target reader 116.

In some examples, the sensor data may be an inductance measurement (L) measured in units of henry (H). Each of the target readers 112, 116 may include a wire coil connected to a LC (inductor/capacitor) resonator. A target reader may include an inductance to digital converter that measures the change in resonant frequency that is caused by a change in inductance, which in turn may be caused by a change in the permeability of the material inside the wire coil. An inductance value L(t) may depend on one or more physical parameters of the coil, including number of turns, length, and cross section. A ratiometric approach may reduce the sensitivity to these parameters. An inductance ratio may be computed a $\beta(t)=L(t)/L_B$, where $L(t)$ is a measured inductance at time t and $L_B$ is a baseline inductance (e.g. an inductance corresponding to a known coil state). A coil state S(t) may have a binary value of "0" if the coil is empty and "1" if the coil is occupied. S(t) is determined to be "1" if β(t) is greater than an upper inductance ratio threshold ($THR_{HI}$) and is determined to be "0" if β(t) is less than a lower inductance ratio threshold ($THR_{LO}$). If $THR_{LO}$<β(t) <$THR_{HI}$, S(t) is determined to be S(t−1) which represents the coil state from the previous sample time. In some examples, the $THR_{LO}$ may be 1.014 and the $THR_{HI}$ may be 1.025.

FIG. 1B illustrates the tool 120 extending within the passage 110 with the target 122 positioned proximal of the proximal target reader 112. Thus, in this configuration, the target 122 may be undetected by the proximal target reader 112 and the distal target reader 116. With reference to FIG. 2A, the period between t0 and t1 may correspond to the configuration of FIGS. 1A and 1B when the target 122 is outside of both the proximal target reader 112 and the distal target reader 116. The occupied or detected state for the proximal target reader 112 may correspond to a measured sensor value 202 approximately equal to the baseline sensor value 206 for the proximal target reader 112 and a measured sensor value 204 approximately equal to the baseline sensor value 208 for the distal target reader 116.

FIG. 1C illustrates the tool 120 extending within the passage 110 with the target 122 positioned within the proximal target reader 112. Thus, in this configuration, the target 122 may be detected by the proximal target reader 112 but not the distal target reader 116. With reference to FIG. 2A, the period between t1 and t2 may correspond to the configuration of FIG. 1C when the target 122 is within the proximal target reader 112 but not within the distal target reader 116. The occupied or detected state for the proximal target reader 112 may correspond to a measured sensor value 202 greater than the baseline sensor value 206 for the proximal target reader 112 and a measured sensor value 204 approximately equal to the baseline sensor value 208 for the distal target reader 116.

Figure 1D:
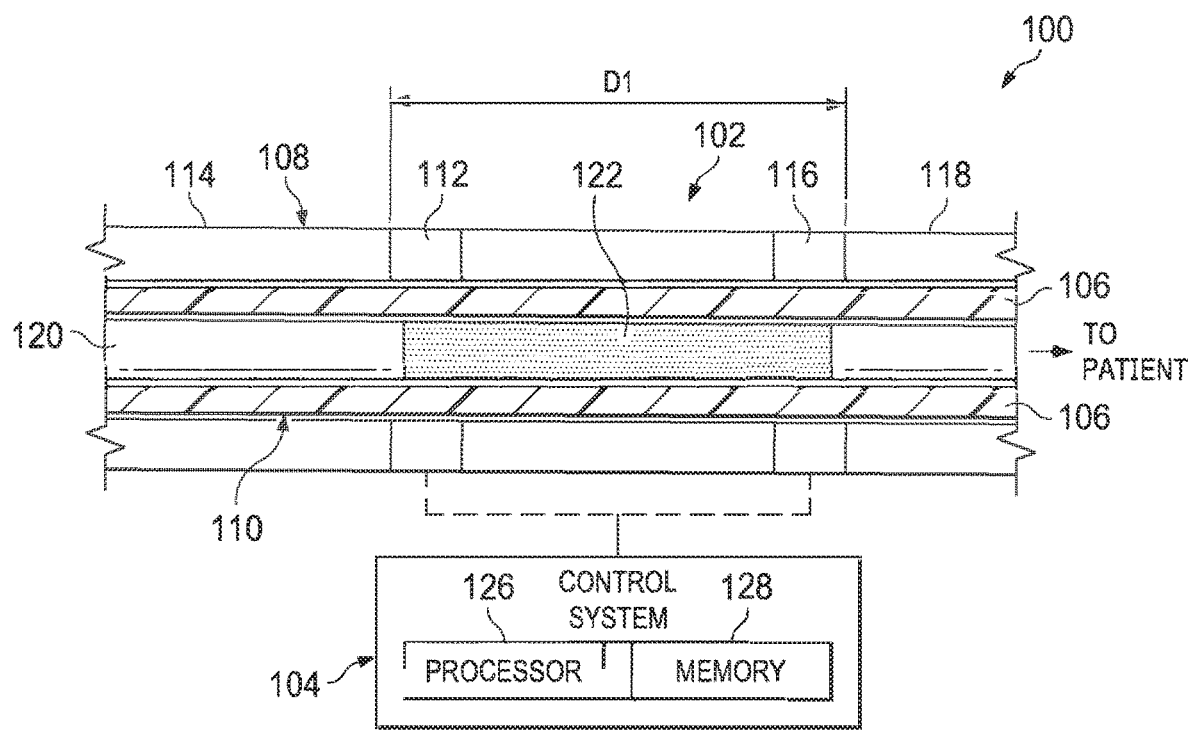

FIG. 1D illustrates the tool 120 extending within the passage 110 with the target 122 positioned within both the proximal target reader 112 and the distal target reader 116. Thus, in this configuration, the target 122 may be detected by both proximal target reader 112 and the distal target reader 116. With reference to FIG. 2A, the period between t2 and t3 may correspond to the configuration of FIG. 1D when the target 122 is within the proximal target reader 112 and within the distal target reader 116. The occupied or detected state for the proximal target reader 112 may correspond to a measured sensor value 202 greater than the baseline sensor value 206 for the proximal target reader 112 and a measured sensor value 204 greater than the baseline sensor value 208 for the distal target reader 116.

Figure 1E:
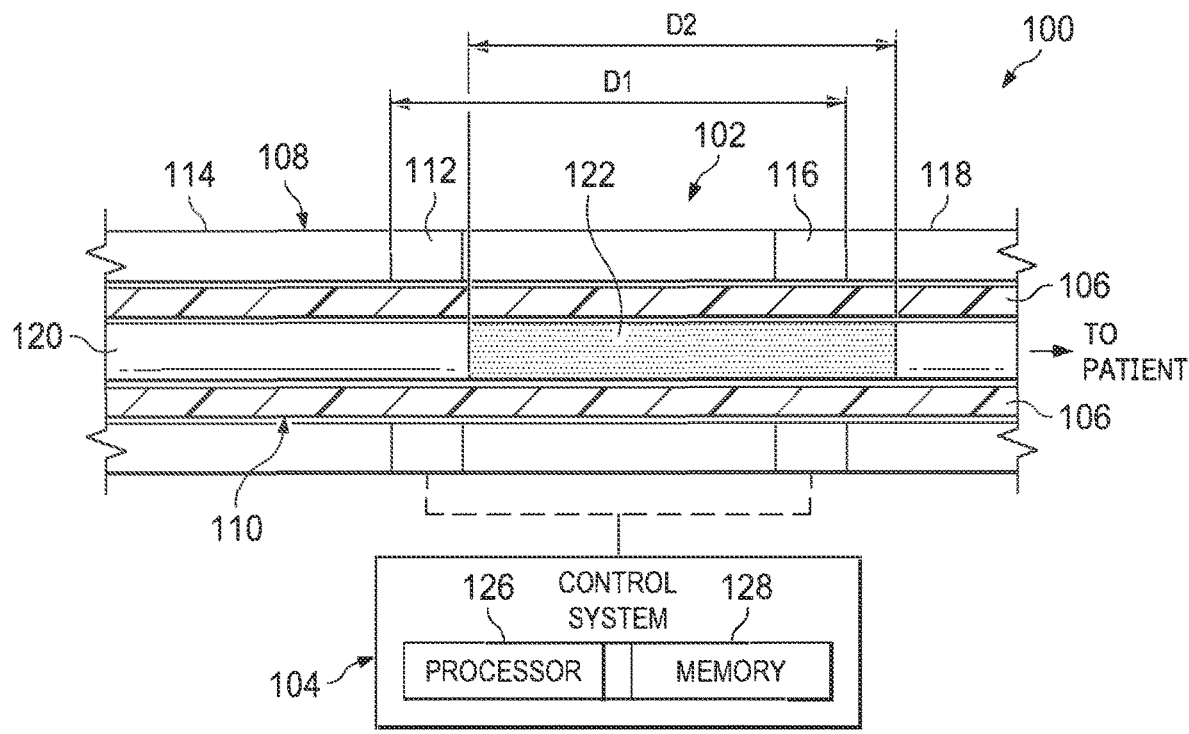

FIG. 1E illustrates the tool 120 extending within the passage 110 with the target 122 positioned within the distal target reader 116 but not within the proximal target reader 112. Thus, in this configuration, the target 122 may be detected by the distal target reader 116 but not the proximal target reader 112. With reference to FIG. 2A, the period between t3 and t4 may correspond to the configuration of FIG. 1E when the target 122 is within the distal target reader 116 but not within the proximal target reader 112. The occupied or detected state for the distal target reader 116 may correspond to a measured sensor value 204 greater than the baseline sensor value 208 for the distal target reader 116 and a measured sensor value 202 approximately equal to the baseline sensor value 206 for the proximal target reader 112. This configuration may also correspond to a fully installed tool configuration.

Figure 2B:
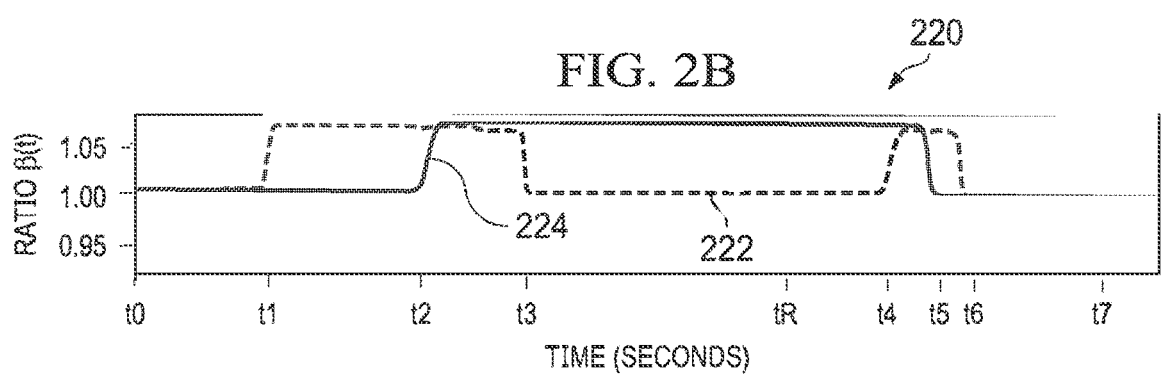
FIG. 2B illustrates a graph of the ratio of the measured sensor values to baseline sensor values according to some examples.

FIG. 2A illustrates the insertion sequence for the period t0 to tR. FIG. 2B also illustrates a retraction sequence for the period tR to t7. In some examples, the retraction sequence may have a shorter duration than the insertion sequence. The period between tR and t4 may correspond to configuration of FIG. 1E where the tool 120 extends within the passage 110 with the target 122 positioned within the distal target reader 116 but not within the proximal target reader 112. The period between t4 and t5 may correspond to configuration of FIG. 1D where the tool 120 extends within the passage 110 with the target 122 positioned within both the distal target reader 116 and the proximal target reader 112. The period between t5 and t6 may correspond to configuration of FIG. 1C where the tool 120 extends within the passage 110 with the target 122 positioned within the proximal target reader 112 but not the distal target reader 116. The period between t6 and t7 may correspond to configuration of FIG. 1B where the tool 120 extends within the passage 110 with the target 122 positioned outside of both the proximal target reader 112 and the distal target reader 116.

Figure 2C:
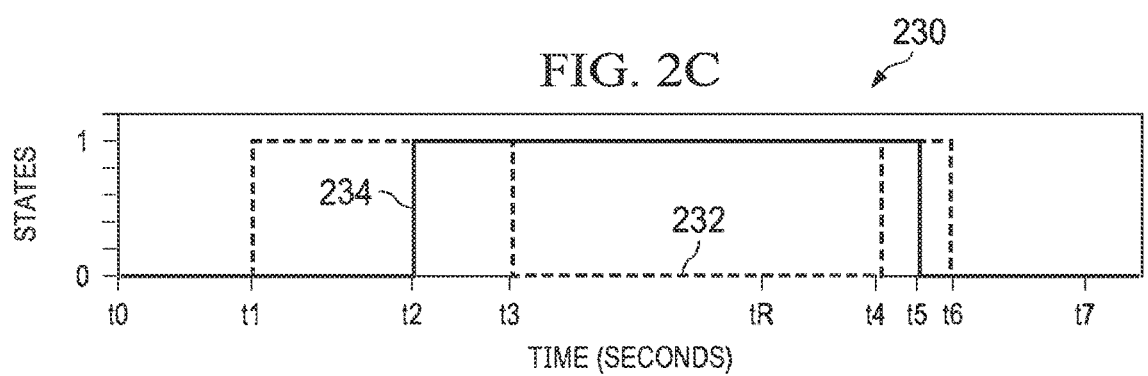
FIG. 2C illustrates a graph, that may be derived from the ratio graph of FIG. 2B, including target reader states for the set of target readers.

FIG. 2B illustrates a graph 220 of the ratio β(t) of the measured sensor values to the baseline sensor values over time. The graph 220 illustrates the calculated ratio 222 for the proximal target reader 112 and the calculated ratio 224 for the distal target reader 116. In this example, if the ratio β(t) is greater than 1 (i.e., the measured inductance is greater than the baseline inductance), the ratio may indicate the presence of the target 122 within the target reader. Accordingly, FIG. 2B illustrates that the proximal target reader 112 senses presence of the target 122 during the period of approximately t1 to t3 and during the period of approximately t4 to t6, and FIG. 2B illustrates that the distal target reader 116 senses presence of the target 122 during the period of approximately t2 to t5. An advantage of determining target presence or absence based on the ratio method may be that it does not require a detailed knowledge of sensor characteristics, such as number of coil turns, length and cross-sectional area of the mounting member 108, that may be difficult to control in manufacturing FIG. 2C illustrates a graph 230, that may be derived from the ratio data of graph 220, including a target reader state 232 for the proximal target reader 112 and a target reader state 234 for the distal target reader 116. The graph illustrates binary states for the target readers with a "0" indicating "no target detected" and a "1" indicating "target detected." Accordingly, FIG. 2C illustrates that the proximal target reader 112 senses the target 122 during the period of approximately t1 to t3 and during the period of approximately t4 to t6, and FIG. 2C illustrates that the distal target reader 116 senses the presence of the target 122 during the period of approximately t2 to t5.

Figure 3:
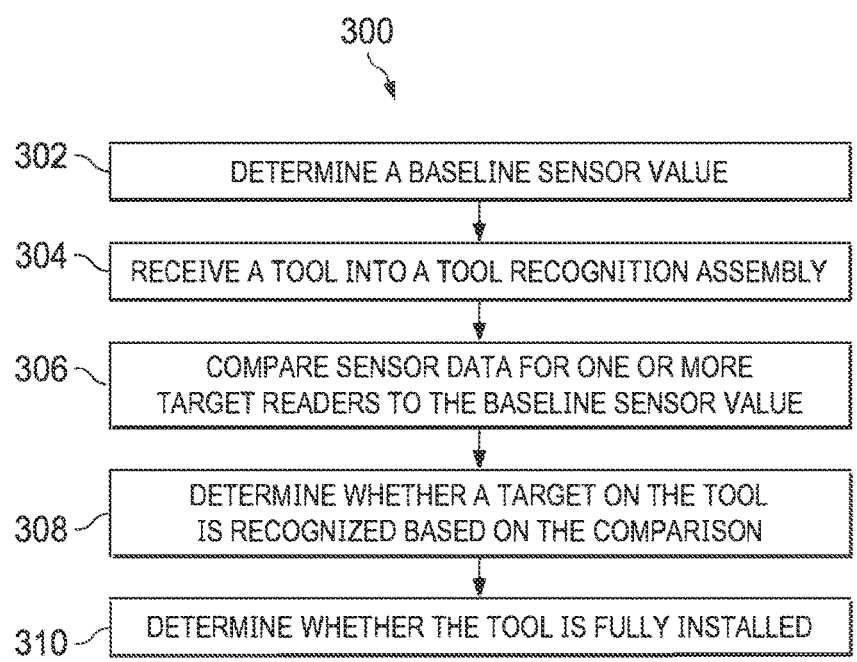
FIG. 3 is a flowchart illustrating a method for determining if a tool is installed in a receiving member according to some examples.

FIG. 3 is a flowchart illustrating an example method 300 for determining if a tool is installed in a receiving member. For example, the method 300 may be used to determine if the tool 120 is fully installed as shown in FIG. 1E. In other examples, the tool 120 may be considered fully inserted when the tool 120 is inserted to such a degree as to permit the tool 120 being used within the body of a patient, inserted to such a degree that a distal end of the tool 120 is within a predetermined distance of a distal end of the receiving member 106, inserted to such a degree that the tool 120 extends through the mounting member 108, inserted such that the distal of the tool 120 is flush with a distal end of the receiving member, inserted to such a degree that a distal portion of the tool 120 extends a predetermined distance past a distal end of the receiving member, or combinations thereof.

At a process 302, a first baseline sensor value is determined. For example and as shown in FIG. 1A, after a set-up process in which the tool recognition assembly 102 and the receiving member 106 are mounted to a platform such as a robot-assisted manipulator assembly, the tool recognition assembly 102 may initiate a latching process in which a baseline value for each of the target readers 112, 116 is determined. Typically, the baseline sensor value is determined when the target readers are unoccupied by the target 122, the tool 120, or other foreign objects. Sometimes an error occurs, and the latching process is performed while the tool 120 or other foreign object is in one or both of the target readers. For example, the tool 120 may be present in the receiving member 106 when the receiving member 106 is inserted into the tool recognition assembly 102, and thus the baseline sensor value after latching will erroneously reflect the presence of the tool 120. A process for correcting a baseline error that results from an erroneous set-up process is described below at FIGS. 4A and 4B.

At a process 304, a tool may be received into a tool recognition assembly. For example and as shown in FIGS. 1B-1E, the tool 120 may be inserted into the tool recognition assembly 102. At a process 306, sensor data from one or more target readers may be compared to the baseline sensor value. For example, the sensor data 202 from the target reader 112 may be compared to the baseline value 206, and the sensor data 204 from the target reader 116 may be compared to the baseline value 208. One type of comparison is the ratio β(t) data 222 and 224 or the state data 232, 234.

At a process 308, a determination may be made as to whether a target on the tool is recognized based on the comparison. For example, the ratio data 222 with values greater than approximately "1" indicates that the target 122 is detected by the target reader 112 between times t1 and t3 and between times t4 and t6, and the ratio data 224 with values greater than approximately "1" indicates that the target 122 is detected by the target reader 116 between times t2 and t5. The ratio data 222 with values of approximately "1" indicates that the target 122 is not detected by the target reader 112 between times t0 and t1, times t3 and t4 and times t6 and t7. The ratio data 224 with values of approximately "1" indicates that the target 122 is not detected by the target reader 116 between times t0 and t2 and between times t5 and t7. Determining whether a sensor value received from a target reader corresponds to a detected target by using a comparison to a baseline value may assume that the target reader is unoccupied by the target 122, the tool 120, or other foreign objects during a latching process. As described below with reference to FIGS. 4A and 4B, sometimes an error occurs, and the latching process is performed while the tool 120 or other foreign object is present in one or both target readers. Correction of such and error is further described with reference to FIG. 5.

At a process 310, a determination may be made as to whether the tool is fully installed. For example, the ratio data 222 and 224 may indicate that the tool is fully installed, as shown in FIG. 1E, during the period t3 to t4. In some examples, detecting whether or not the tool 120 is fully inserted (or otherwise acceptably positioned for operation may comprise comparing sensor data from the target readers 112, 116 to a pre-established model insertion signature. As used herein, "pre-established model insertion signatures" or "model insertion signatures" refer to insertion signatures that have been generated by a modeling software application, inputs from a user interface, measurements logged during an installation of another tool, etc. that have been established to represent positions of a tool while being inserted into the tool recognition assembly. The tool 120 may be determined to be acceptably positioned for operation and thus fully inserted when a sequence of sensor data from the target readers 112, 116 match the model insertion signature indicating a fully inserted tool and may be determined not to be acceptably positioned for operation and thus not fully inserted when readings from the target readers 112, 116 do not match the model insertion signature indicating a fully inserted tool. The sensor data from target readers 112, 116 that correspond to the model insertion signature indicating a fully inserted tool can include various characteristics, such as a sequence of sensor data from the target readers 112, 116 (e.g., sensor data 202, 204), a sequence of ratio β(t) data for the target readers 112, 116 (e.g., the ratio data 222, 224), a sequence of status data for the target readers 112, 116 (e.g., state data 232, 234), a threshold duration of target readings by the target readers 112, 116, or combinations data values from the target readers 112, 116.

The method 300 is not limited to determining installation for a single tool or a single classification of tool. The systems and methods described herein may be used to detect installation of more than one tool or type of tools, including imaging tools, investigation tools such as biopsy tools, and/or treatment tools such as ablation tools. For example, inductance-based sensing may be adapted to support recognition of multiple tools simultaneously. As an example, an upper inductance ratio threshold $THR_{HI}$ of 1.025 may be associated with an imaging tool, and an upper inductance ration threshold $THR_{HI}$ of 1.080 may be associated with an ablation tool. For a sensed inductance ratio of 1.030, the system may detect the presence of an imaging tool because the ratio of 1.030 exceeds the imaging tool threshold ratio of 1.025 but is substantially below (or a predetermined amount below) the ablation tool threshold ratio of 1.080. If the sensed inductance ratio is 1.100, the system may detect the presence of an ablation tool because the ratio 1.100 exceeds the ablation tool threshold ratio of 1.080.

Figure 4A:
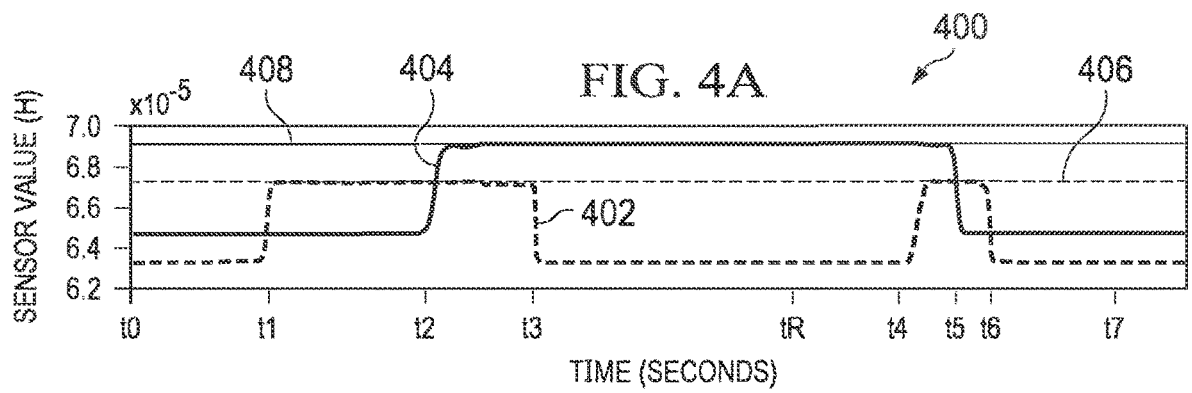
FIG. 4A illustrates a graph of measured sensor values of a set of target readers of a tool recognition system with erroneous baseline sensor values, according to some examples.

Determining whether a sensor value received from a target reader corresponds to a detected target by comparison to a baseline value at process 308 may assume that the target reader is unoccupied by the target 122, the tool 120, or other foreign objects during a latching process. Sometimes an error occurs, and the latching process is performed while the tool 120 or other foreign object is present in one or both target readers. FIG. 4A illustrates a graph 400 of the measured sensor values of the target readers 112, 116 over time. In some examples, the sensor measurement may be an inductance measurement (L) measured in units of henry (H). The graph 400 illustrates the sensor data 402 from the proximal target reader 112 and sensor data 404 from the distal target reader 116 as the tool 120 is inserted and retracted from the tool recognition assembly 102. A baseline value 406 is latched or registered for the proximal target reader 112, and a baseline value 408 is latched or registered for the distal target reader 116. Without further data analysis, it may be unclear from the data 402, 404 that the latched baseline values do not correspond to unoccupied or absent readings from the target readers 112, 116. Rather, the latched baseline values correspond to occupied or present readings from the target readers 112, 116. This error may occur, for example, if the tool 120, the target 122, or foreign objects are present in the passage 110 during the set-up process when process in which the tool recognition assembly 102 and the receiving member 106 are mounted to a platform such as a robot-assisted manipulator assembly. The sensor data 402, 404 may have the same inductance values as the sensor data 202, 204, respectively, and thus an analysis of the sensor data 402, 404 alone may not indicate that the latched baseline values 406, 408 do not correspond to unoccupied or absent readings from the target readers 112, 116. An analysis of the ratio β(t) values, however may identify the error.

Figure 4B:
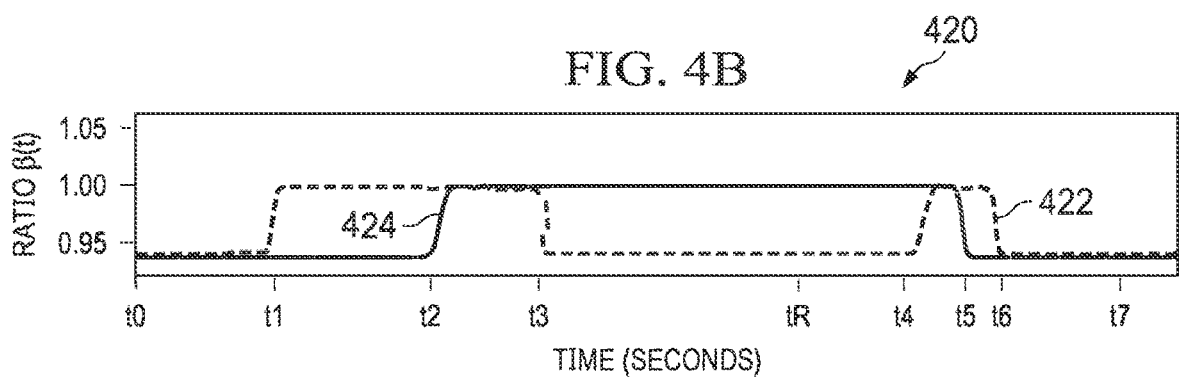
FIG. 4B illustrates a graph of the ratio of the measured sensor values to the erroneous baseline sensor values, according to some examples.

FIG. 4B illustrates a graph 420 of the ratio β(t) of the measured sensor value to the baseline sensor value over time as a tool 120 is inserted and retracted through a tool recognition assembly 102. The graph 420 illustrates the calculated ratio 422 for the proximal target reader 112 and the calculated ratio 424 for the distal target reader 116. In this example, the ratio β(t) is less than 1 for the period t0 to t1, the period t3 to t4, and the period after t6 for target reader 112. The ratio β(t) is less than 1 for the period t0 to t2 and the period after t5. During these periods the measured inductance is less than the baseline inductance which may indicate that the baseline sensor values are in error. As the tool 120 is inserted through the tool recognition assembly 102 during the period from t0 to tR, the ratio does not rise above 1, which may also indicate that the baseline sensor values are in error. The recognition of the error condition may result in the reversal of the tool at time tR. Prior methods for correcting the error condition have involved removing the tool 120, the tool recognition assembly 102, and/or the receiving member 106 from the platform (e.g., a robot-assisted manipulator assembly) and repeating a set-up process. In the correction method described below at FIG. 5, the baseline sensor value may be corrected by retraction and reinsertion of the tool without significant disruption to the workflow caused by removing and reattaching the tool recognition assembly.

Various properties of the sensor data detected by the target readers 112, 116 may affect the determination of whether a particular reading from the target readers 112, 116 may contribute to a detected insertion signature. For example, the strength (i.e. whether the measured sensor value exceeds a detection threshold), duration, multiple thresholds, or a combination of strength, duration, and multiple thresholds of the readings can be used to determine when a target is detected by the target readers 112, 116. Additionally or alternatively, derivative properties of the signals read by the target readers 112, 116 such as the rate of change of the signal (e.g., slope), may be used in the determination of a detected insertion signature. When an inductive element is used as the target 122, the target readers 112, 116 can produce an inductance measurement signal that varies as the target 122 approaches the target reader, as the target 122 is proximate the target readers 112, 116, and as the target 122 moves away from the target readers 112, 116. An amplitude (or strength) of the inductance measurement can indicate a presence of a target 122 in a detection zone of the target readers 112, 116. The strength (i.e. amplitude threshold) of the inductance measurement, duration of the inductance measurement, multiple thresholds, and a combination of strength, duration of the inductance measurement, and multiple thresholds read by the target readers 112, 116 can be used to determine whether the target 122 has been detected in the detection zone of the target reader 112, 116. Additionally, a slope, inductance ratios, and/or other derivatives of the inductance measurement signal can be used to indicate a presence or an absence of the target in the detection zone of a target reader 112, 116. One way to represent the target detection and non-detection respectively is to use a binary (e.g., '1' or '0') signal to indicate the presence or absence of a target in the detection zone of the respective target reader 406, 407 as determined by the strength, duration, slope, ratios, and combinations thereof of the inductance measurement signal as well as other derivatives of the inductance measurement signal from the target readers 112, 116.

Figure 5:
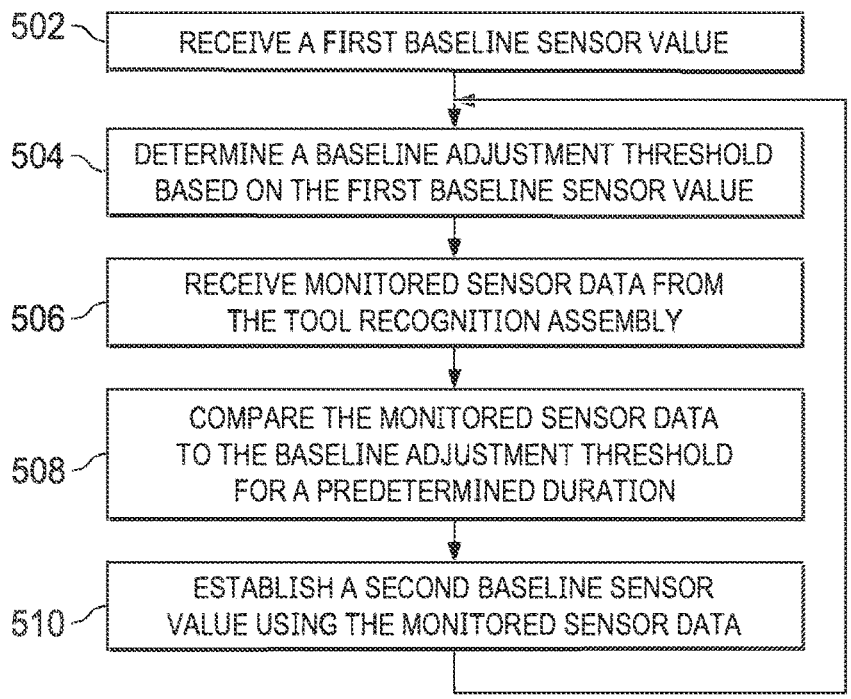
FIG. 5 is a flowchart illustrating a method for adjusting a baseline sensor value according to some examples.

FIG. 5 is a flowchart illustrating an example method 500 for adjusting a baseline sensor value. Method 500 provides a process for correcting a baseline error that may result from an error in the set-up process. Correcting the error using method 500 may be more efficient than decoupling the tool 120, the tool recognition assembly 102 and/or the receiving member 106 from the robot-assisted manipulator assembly and repeating the set-up process. At a process 502, a first baseline value may be received. For example, after a set-up process in which the tool recognition assembly 102 and the receiving member 106 are mounted to a platform such as a robot-assisted manipulator assembly, the tool recognition assembly 102 may initiate a latching process in which a baseline value for the target reader 116 is determined. In this example, the baseline value latches when the target reader 116 is occupied by the target 122, the tool 120, or another foreign object, thus generating the erroneous baseline value. FIG. 6A illustrates a graph 600 of the measured sensor values of the target reader 116 during the period t4 to t7 when a downward baseline adjustment occurs. The graph 600 illustrates the sensor data 404 from the distal target reader 116. The initial inductive baseline value 408 is latched or registered for the distal target reader 116.

At a process 504, a downward baseline adjustment threshold is determined based on the first baseline sensor value. For example and with reference to FIG. 6A, a downward baseline adjustment threshold 610 is an inductance threshold that may be determined by dividing the initial baseline value 608 by the upper inductance ratio threshold (e.g. $THR_{HI}$=1.025) plus a robustness margin (e.g. a value in the range 0.005 to 0.025). Thus, in this example the downward adjustment threshold 610 is computed as (the initial baseline value 608)/(1.025+0.020).

At a process 506, monitored sensor data may be received from the tool recognition assembly. For example, the inductive data 404 which may be instantaneous inductance values from the target reader 116 may be received and monitored as the tool 120 is inserted into the tool recognition assembly 102. As described above, if tool 120 is inserted through the tool recognition assembly 102 and the ratio β(t) does not rise above 1, an error with the baseline sensor values may be indicated. The recognition of the error condition may result in the retraction of the tool beginning at time tR. In some examples, the insertion time t0 to tR may be longer than the retraction time tR to t7.

At a process 508, the monitored sensor data may be compared to the baseline adjustment threshold for a predetermined duration. For example, the instantaneous inductive data 404 may begin to drop at approximately t=t5a and may cross the baseline adjustment threshold 610 at approximately t=t5. A monitoring window $T_{AVG}$ may begin when the inductive data 404 drops below the baseline adjustment threshold 610. In some embodiments the monitoring window $T_{AVG}$ may have a duration that is, for example, sufficiently long to establish confidence that the measured inductance is remaining below the baseline adjustment threshold 610. In some examples, a monitoring window $T_{AVG}$ may have a duration of between 0.5 seconds and 1.0 seconds.

At a process 510, if a comparison criterion is satisfied, an adjusted or second baseline sensor value may be established using the monitored sensor data. In some examples, the comparison criterion may be whether the monitored sensor data remains below the baseline adjustment threshold for the predetermined duration. If so, the adjusted baseline sensor value may be lower than the initial baseline sensor value. In some examples, the comparison criterion may be whether the average of the monitored sensor data is below the baseline adjustment threshold for the predetermined duration. If so, the adjusted baseline sensor value may be lower than the initial baseline sensor value. In some examples, the comparison criterion may be whether a ratio of the monitored sensor data to the baseline adjustment threshold is lower than 1 for the predetermined duration. If so, the adjusted baseline sensor value may be lower than the initial baseline sensor value. In some examples, the comparison criterion may be whether the monitored sensor data is greater than the baseline adjustment threshold for the predetermined duration. If so, the adjusted baseline sensor value may be greater than the initial baseline sensor value. In some examples, the adjusted baseline sensor value may be an average of the measured sensor data during the duration of the monitoring window.

For example, if the measured inductance at the target reader 116 remains below the baseline adjustment threshold 610 for the duration of the monitoring window $T_{AVG}$, the adjusted baseline value 612 may be established at time t7. The adjusted baseline value 612 may be established as the average inductance value over the monitoring window $T_{AVG}$. The value of the adjusted baseline value may be expressed as:

$$L_{B,new} \text{ (e.g., adjusted baseline value 610)} = \frac{T_{ker}}{T_{AVG}} \sum_{t_{start}}^{t_{end}} L(t) = \sum_{n_{start}}^{n_{end}} L(n)$$

where $T_{ker}$ is the kernal servo period, $t_{start}$ and $t_{end}$ are the time boundaries of the adjustment window and $n_{start}$, $n_{end}$ are the corresponding kernal cycles.

Because the monitoring window $T_{AVG}$ includes measured inductance during the period between t5 and t5b when the inductance values are ramping down, the adjusted baseline value 612 may be higher than the relatively steady inductance values during the period after t5b. Accordingly, the window used for averaging the inductance values may be delayed such that the window begins after the ramp down has been completed. In this example, the monitoring window $T_{ALT}$ for calculating an adjusted baseline value 614 may begin at t5b. The adjusted baseline value 614 may be the average inductance value during the window $T_{ALT}$. In some examples, use of the monitoring window $T_{ALT}$ may allow the baseline adjustment threshold 610 to be raised slightly to allow for more prompt detection of the need to lower the baseline value.

FIG. 6B illustrates a graph 620 of the ratio β(t) of the measured sensor value to the baseline sensor value over a period during which a downward adjustment of the baseline value occurs. The graph 620 illustrates the calculated ratio 622 for the distal target reader 116. In this example, the ratio β(t) is less than 1 for the period t5a to t7, indicating an error in the establishment of the baseline value and indicating that the ratio β(t) is not an accurate guide for determining whether a target is present or absent in the target reader 116. At the end of the $T_{AVG}$ or $T_{ALT}$ window, the baseline value is adjusted and, beginning at time t7, the ratio β(t) has a value of 1 or greater than 1. As adjusted, the ratio β(t) may be used to determine whether the target is present or absent in the target reader 116.

The method 500 may allow a user to adjust a baseline value by inserting and retracting the tool 120 and may avoid the need to repeat the set-up process, including removing and re-mounting the tool recognition assembly 102 and the receiving member 106 to the robot-assisted manipulator assembly.

In some examples, after the process 510 establishes a new baseline value, the processes 504-510 may be repeated, thus determining a new baseline adjustment threshold and allowing further adjustment of the baseline value if the monitored sensor values drop below the new baseline adjustment threshold. In some examples, a downward adjustment of the baseline value may be triggered by the proximal target reader 112 as the tool 120 is inserted, when the proximal target reader 112 transitions from occupied to empty. A subsequent baseline adjustment may occur when the tool 120 is retracted and the proximal target reader 112 transitions from empty to occupied. In some examples, a downward adjustment of the baseline value may be triggered by the distal target reader 116 as the tool 120 is retracted and transitions from occupied to empty, but no further baseline adjustment would be triggered until the instrument 112 is re-inserted.

In some examples, the initial baseline latching may occur when one of the target readers is occupied and the other is not. For example, the initial baseline latching may occur while the distal target reader 116 is empty and the proximal target reader 112 is occupied. In this example, the distal target reader 116 may transition to an occupied state as expected. The proximal target reader 112 may appear to stay at empty state until the baseline value is adjusted and will subsequently transition to an occupied state as the tool 120 is retracted.

In some examples an upward baseline adjustment may be performed in a manner similar and symmetrical to the downward adjustment described for method 500. An erroneously low initial baseline value may result, for example, from transient electromagnetic noise at the time of inductance latching or from fluid contamination of the inductive coils of the target readers. While upward baseline value adjustment may improve detection of expected state transitions (e.g., if the baseline value is too low, the target readers may indicate an "occupied" state regardless of whether the target is actually present) and may improve robustness to a wider variety of instruments, it may also reduce the chance of correctly detecting that a target is present in a target reader. FIG. 7 illustrates a graph 700 of the measured sensor values 702 of a target reader during a period when an upward baseline adjustment occurs. As shown, an initial baseline value 704 may be adjusted upward to an upward adjusted baseline 706 if the inductance value persists above an upward adjustment threshold 708 for a period $T_{AVG}$. In some examples, the upward baseline adjustment threshold 708 is an inductance threshold that may be determined by multiplying the initial baseline value 608 by the upper inductance ratio threshold (e.g. $THR_{HI}$=1.025) plus a margin of error (e.g. 0.005–0.025). In this example the upward adjustment threshold 708 is computed as (the initial baseline value 608)×(1.025+0.010). In some examples, the baseline value may not be adjusted upward unless both target readers are simultaneously in an empty state. In some examples, the upward adjustment threshold may be determined as a fraction of the latched baseline value. In the case up an upward baseline adjustment, an algorithm for determining the upward baseline adjustment may continue to run even after the upward baseline has occurred. The new baseline value may be computed in the most recent time window for which the inductance has been above the baseline adjustment threshold. The baseline adjustment threshold for upward adjustment may be fixed and the baseline adjustment threshold for downward adjustment may be changed each time the baseline value is updated.

Because any of a variety of types of tools may be erroneously placed within the receiving member when the initial baseline value is latched, the method 500 is not limited to adjusting a baseline sensor value for a single tool or a single classification of tool. The systems and methods described herein may be used to identify tool detection errors and make correction regardless of the tool or other unexpected objects that generate the error. For example, the inductance ratio threshold associated with each of a variety of tools or classification of tools may be used to determine an associated baseline adjustment threshold which may, in turn, be used to detect a baseline value error and adjust the baseline value, as described.

Figure 8:
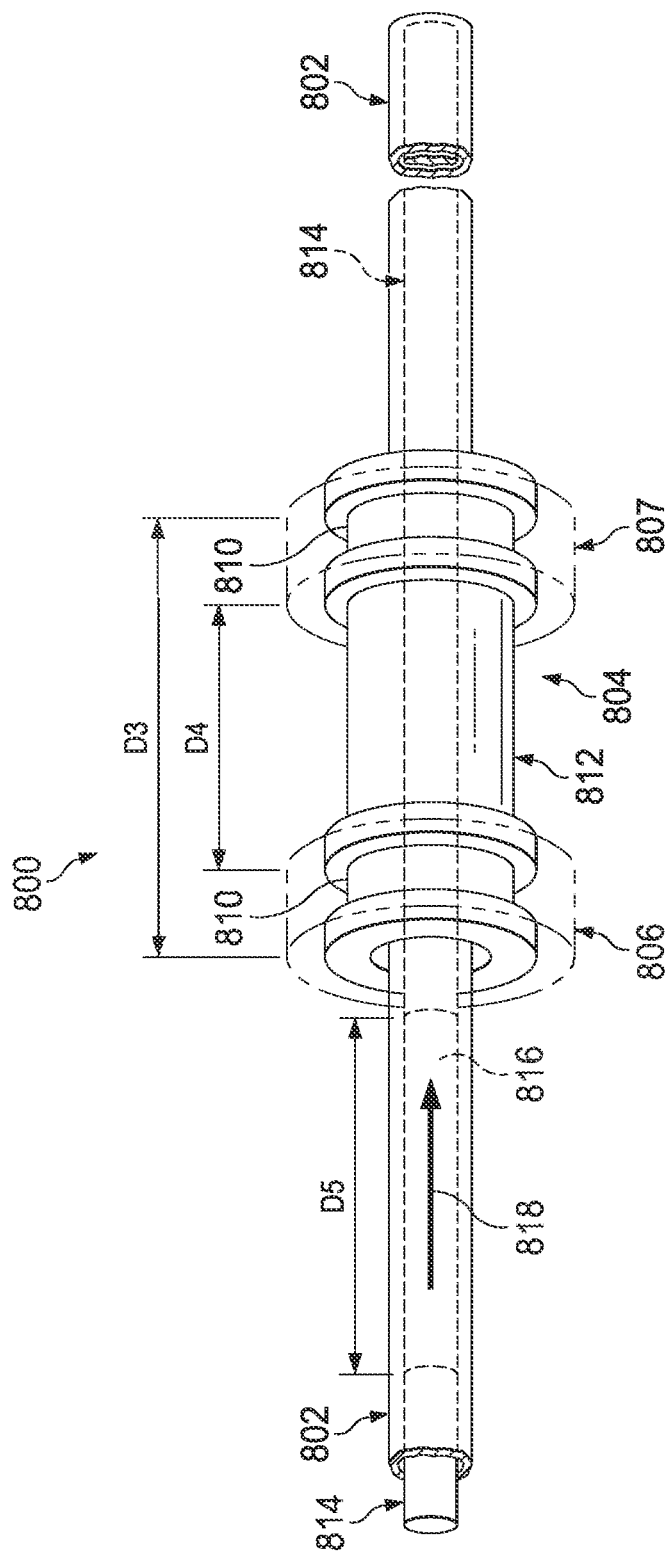
FIG. 8 illustrates a perspective view of a tool recognition assembly according to some examples.

FIG. 8 illustrates a perspective view of a tool recognition assembly 800 that may be implemented as the tool recognition assembly 102 and may be used in any of the methods described herein. FIG. 8 illustrates the tool recognition assembly 800 into which a receiving member 802 (e.g., receiving member 106, a catheter, or other elongate device) may extend. In this embodiment the tool recognition assembly 800 includes a mounting member 804. In various embodiments, the mounting member 804 may be mounted to a manipulator assembly as described in greater detail in FIG. 9. The tool recognition assembly 800 can incorporate one or more target readers configured to detect one or more targets on a tool and/or catheter. In the example shown in FIG. 8, a target reader 806 is coupled to a proximal end of the mounting member 804, and another target reader 807 is coupled to a distal end of the mounting member. In this embodiment, the mounting member 804 is shown as a cylinder or bobbin with channels 810 separated by an elongated body 812. The mounting member 804 may be formed of a plastic, a ceramic, or another type of material that minimizes interference with the target readers 806, 807. Each of the target readers 806, 807 extends into a corresponding one of the channels 810 to couple to the mounting member 804. A distance D3 may span a length between the outer sensing bounds of the target readers 806, 807. A distance D4 may span a length between the inner sensing bounds of the target readers 806, 807. The target readers 806, 807 may comprise an inductive sensor (e.g., an inductor or inductive coil that detects a change in inductance caused by ferromagnetic and conductive properties of a material), a capacitive sensor, a Hall effect sensor, a photogate sensor, an optical sensor, a magnetic switch, a barcode scanner, a radio frequency identification (RFID) scanner, a relative position sensor, or combinations thereof that are capable of reading corresponding one or more targets on a tool to be inserted into the receiving member 802 of the tool recognition assembly 800. Any combination of different types of target readers may be implemented in the tool recognition assembly 800.

In this example, an exemplary tool 814 (e.g., tool 120) may include a target 816 that can be read by the one or more target readers 806, 807 on the tool recognition assembly 800. The target may have a length D5. The length D4 may have a predetermined relationship to the distances D3, D4. For example, the length D4 may be shorter than the length D3 but longer than the length D4 so that the target 816 may concurrently extend within both target readers 806, 807. In some examples, the length D5 may be the same as or longer than length D3. The tool 814 is sized for insertion into the mounting member 804 and receiving member 802 along an insertion trajectory path 818. The tool 814 may extend through the mounting member 804 and receiving member 802.

In the embodiment of FIG. 8, the mounting member 804 includes two channels 810 and may therefore accommodate two target readers 806, 807—one in each channel 810. In alternative embodiments, a mounting member may comprise any number of channels and may accommodate any number of target readers. In some embodiments, the mounting member may lack channels but may nevertheless accommodate any number of target readers via other coupling mechanisms. In some embodiments, there may be fewer target readers than channels, where some channels can be empty. In some embodiments, the mounting member may have a non-cylindrical shape and may be any type of bracket or mounting mechanism for mounting one or more target readers in a location proximate to the receiving member. In some embodiments, the receiving member may have an open channel or any shape for receiving and allowing longitudinal movement of a tool. In some embodiments, the mounting member (or regions of the reader mount) may be considered to be an element or elements of one or more of the target readers in that the mounting member may play a role in the detection of one or more targets on the tool. For example, the channels may be of a different composition than the rest of the mounting member and may facilitate detection of one or more targets on the tool. In the embodiment of FIG. 8, the tool 814 may include any number of targets positioned along the length of the tool. There may be a different number of targets than there are target readers.

Figure 9:
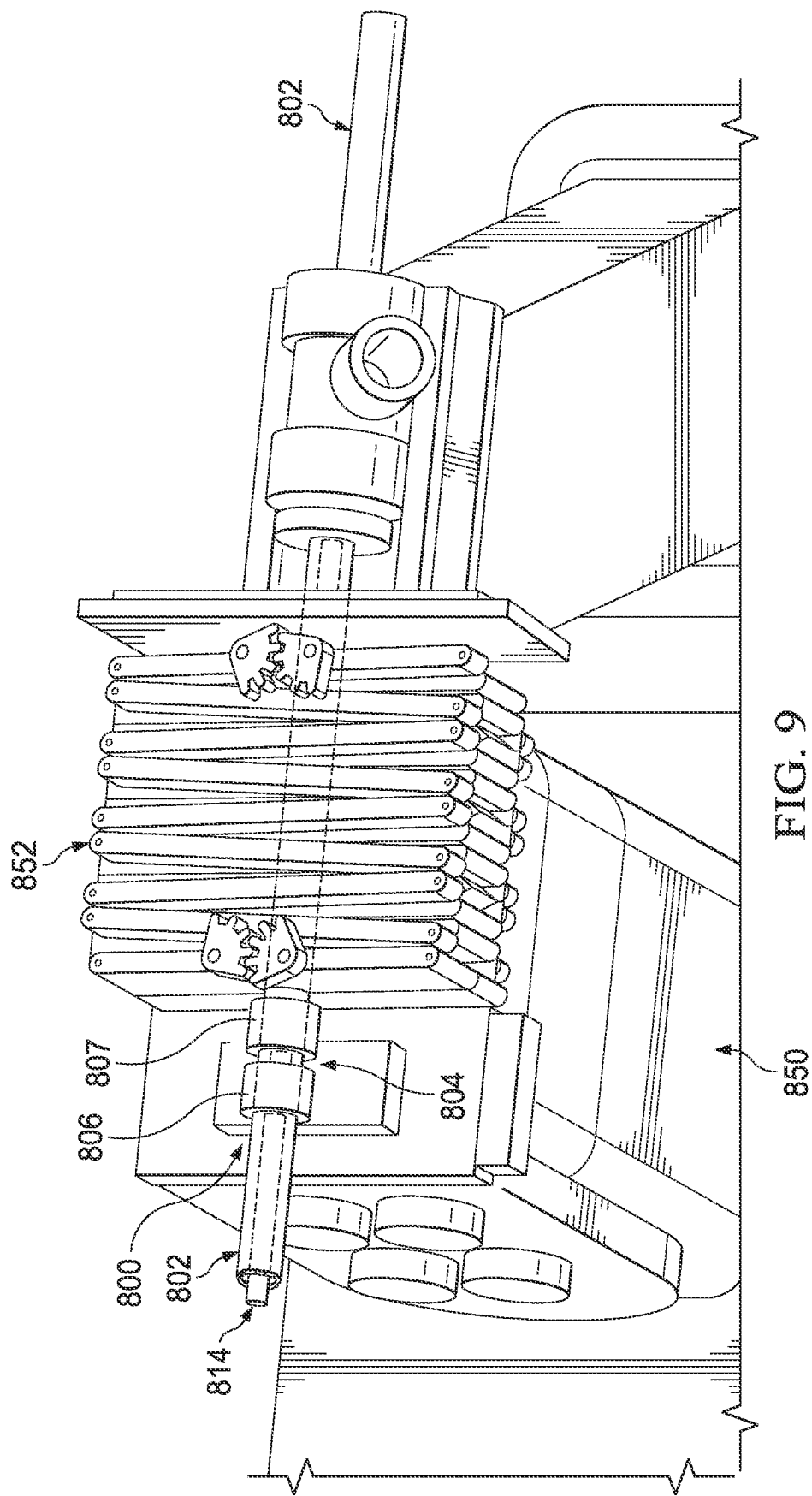
FIG. 9 illustrates the tool recognition assembly coupled to an instrument carriage of a robot-assisted manipulator assembly, according to some examples.

FIG. 9 illustrates the tool recognition assembly 800 coupled to an instrument carriage 850 of a robot-assisted manipulator assembly. In alternative embodiments, the tool recognition assembly 800 may be coupled to manual manipulators or other structures used for receiving a tool. In FIG. 9, the tool recognition assembly 800 is coupled to the instrument carriage 850 proximal of an expandable support structure 852 that may be used to support an extended length of the receiving member 802 outside of the patient anatomy. For example, the tool recognition assembly 800 may be press fit onto a proximal mount (not shown) on the expandable support structure 852.

In some embodiments, a tool recognition assembly or other tool detection sensors may be located in other locations. For example, the target readers may be located on a quick connect coupling between a vision probe and a catheter or on a motor pack of the teleoperational manipulator assembly. In some embodiments, a tool recognition assembly may recognize that a tool is absent from a tool holder, thus indicating that the tool may be in another location such as the catheter.

Figure 10:
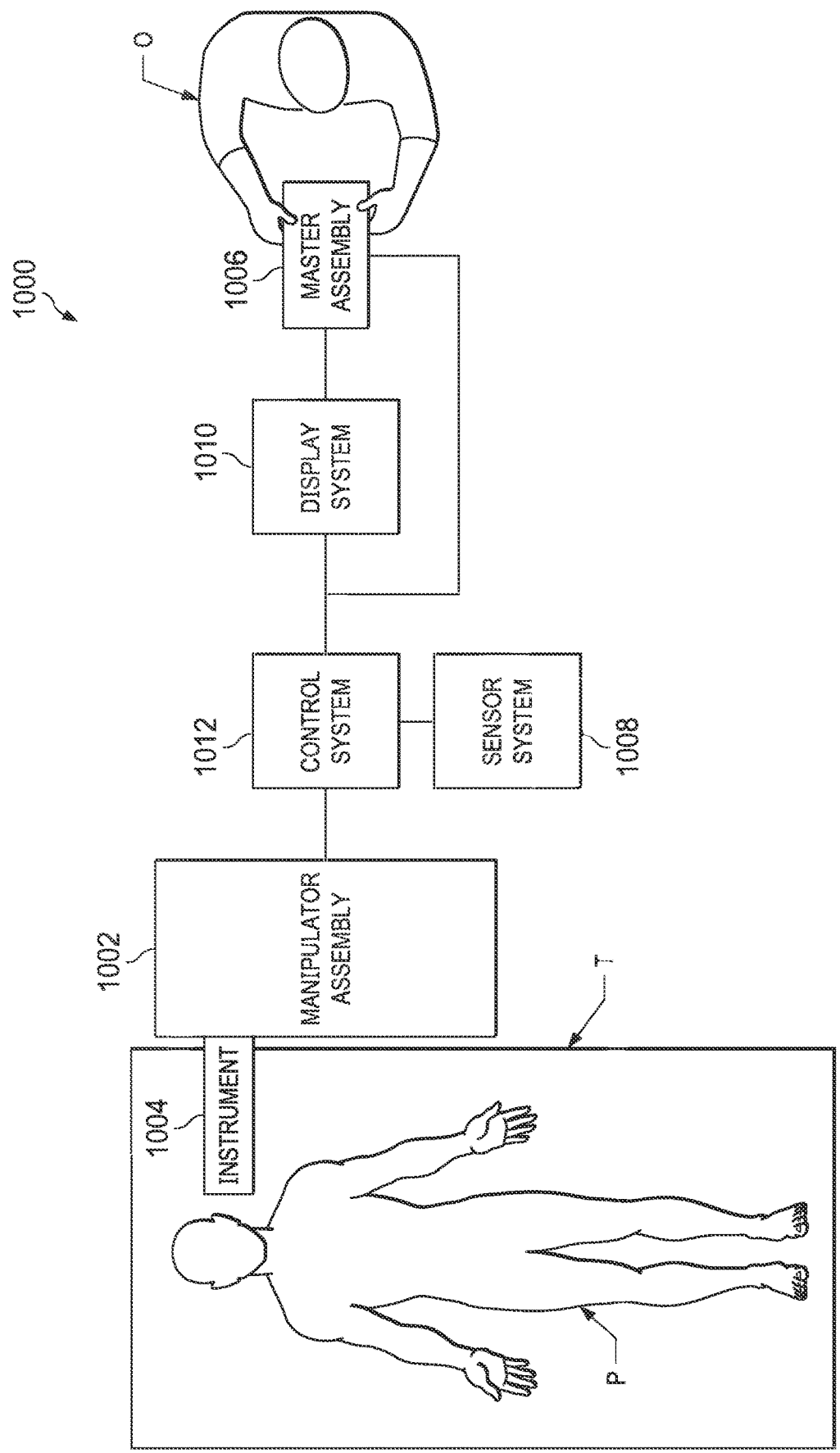
FIG. 10 illustrates a robot-assisted medical system, according to some examples.

In some embodiments, the systems and methods disclosed herein may be used in a medical procedure performed with a robot-assisted medical system as described in further detail below. As shown in FIG. 10, a robot-assisted medical system 1000 may include a manipulator assembly 1002 for operating a medical instrument 1004 in performing various procedures on a patient P positioned on a table T in a surgical environment. The medical instrument 1004 may correspond to the tool 120, or any tool or instrument described herein. The manipulator assembly 1002 may be robot-assisted, non-robot assisted, or a hybrid assembly with select degrees of freedom of motion that may be motorized and/or robot-assisted and select degrees of freedom of motion that may be non-motorized and/or non-robot assisted. A master assembly 1006, which may be inside or outside of the surgical environment, generally includes one or more control devices for controlling manipulator assembly 1002. Manipulator assembly 1002 may include an instrument carriage or other support member that supports medical instrument 1004 and may optionally include a plurality of actuators or motors that drive inputs on medical instrument 1004 in response to commands from a control system 1012. The actuators may optionally include drive systems that when coupled to medical instrument 1004 may advance medical instrument 1104 into a naturally or surgically created anatomic orifice. Other drive systems may move the distal end of medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 1004 for grasping tissue in the jaws of a biopsy device and/or the like.

Robot-assisted medical system 1000 also includes a display system 1010 for displaying an image or representation of the surgical site and medical instrument 1004 generated by a sensor system 1008 which may include an endoscopic imaging system. Display system 1010 and master assembly 1006 may be oriented so an operator O can control medical instrument 1104 and master assembly 1006 with the perception of telepresence.

In some embodiments, medical instrument 1004 may include components for use in surgery, biopsy, ablation, illumination, irrigation, or suction. Optionally medical instrument 1004, together with sensor system 1008 may be used to gather (e.g., measure or survey) a set of data points corresponding to locations within anatomic passageways of a patient, such as patient P. In some embodiments, medical instrument 1004 may include components of the imaging system which may include an imaging scope assembly or imaging instrument that records a concurrent or real-time image of a surgical site and provides the image to the operator or operator O through the display system 1010. In some embodiments, imaging system components may be integrally or removably coupled to medical instrument 1004. However, in some embodiments, a separate endoscope, attached to a separate manipulator assembly may be used with medical instrument 1004 to image the surgical site. The imaging system may be implemented as hardware, firmware, software or a combination thereof which interact with or are otherwise executed by one or more computer processors, which may include the processors of the control system 1012.

The sensor system 1008 may include a position/location sensor system (e.g., an electromagnetic (EM) sensor system) and/or a shape sensor system for determining the position, orientation, speed, velocity, pose, and/or shape of the medical instrument 1104.

Robot-assisted medical system 1000 may also include control system 1012, which may include the control system 104. Control system 1012 includes at least one memory and at least one computer processor for effecting control between medical instrument 1004, master assembly 1006, sensor system 1008, and display system 1010. Control system 1012 also includes programmed instructions (e.g., a non-transitory machine-readable medium storing the instructions) to implement a plurality of operating modes of the robot-assisted medical system including a navigation planning mode, a navigation mode, and/or a procedure mode. Control system 1012 also includes programmed instructions (e.g., a non-transitory machine-readable medium storing the instructions) to implement some or all of the methods described in accordance with aspects disclosed herein, including, for example, moving a mounting bracket coupled to the manipulator assembly to the connection member, processing sensor information about the mounting bracket and/or connection member, and providing adjustment signals or instructions for adjusting the mounting bracket.

Control system 1012 may optionally further include a virtual visualization system to provide navigation assistance to operator O when controlling medical instrument 1004 during an image-guided surgical procedure. Virtual navigation using the virtual visualization system may be based upon reference to an acquired pre-operative or intra-operative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. The methods described herein may be illustrated as a set of operations or processes. The processes may be performed in a different order than the order shown, and one or more of the illustrated processes might not be performed in some embodiments. Additionally, one or more processes that are not expressly illustrated may be included before, after, in between, or as part of the illustrated processes. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like. While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

This disclosure describes various instruments, portions of instruments, and anatomic structures in terms of their state in three-dimensional space. As used herein, the term position refers to the location of an object or a portion of an object in a three-dimensional space (e.g., three degrees of translational freedom along Cartesian x-, y-, and z-coordinates). As used herein, the term orientation refers to the rotational placement of an object or a portion of an object (e.g., in one or more degrees of rotational freedom such as roll, pitch, and/or yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

While certain illustrative embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system, comprising:
a tool recognition assembly;
a receiving member for receiving a tool; and
a control system in communication with the tool recognition assembly, wherein the control system comprises:
 a processor; and
 a memory comprising machine-readable instructions that, when executed by the processor, cause the control system to:
  receive a first baseline sensor value from the tool recognition assembly subsequent to a set-up process of the tool recognition assembly and the receiving member;
  determine a baseline adjustment threshold based on the first baseline sensor value;
  receive first monitored sensor data from the tool recognition assembly as the tool is inserted into the receiving member;
  compare the first monitored sensor data to the baseline adjustment threshold for a predetermined duration;
  if the comparison satisfies a comparison criterion for the predetermined duration, establish a second baseline sensor value using the first monitored sensor data; and
  determine if the tool is fully inserted within the receiving member using the second baseline sensor value.

2. The medical system of claim 1, wherein the comparison criterion is the first monitored sensor data is lower than the baseline adjustment threshold for the predetermined duration and wherein the second baseline sensor value is lower than the first baseline sensor value.

3. The medical system of claim 1, wherein the comparison criterion is the first monitored sensor data is greater than the baseline adjustment threshold for the predetermined duration and wherein the second baseline sensor value is higher than the first baseline sensor value.

4. The medical system of claim 1, wherein the comparison criterion is that a ratio of first monitored sensor data to the baseline adjustment threshold is lower than 1 for the predetermined duration and wherein the second baseline sensor value is lower than the first baseline sensor value.

5. The medical system of claim 1, wherein the second baseline sensor value is established as an average of the first monitored sensor data over at least a portion of the predetermined duration during which the first monitored sensor data has passed the baseline adjustment threshold.

6. The medical system of claim 1, wherein the machine-readable instructions, when executed by the processor, further cause the control system to:
determine a second baseline adjustment threshold based on the second baseline sensor value and comparing second monitored sensor data to the second baseline adjustment threshold.

7. The medical system of claim 1, further comprising the tool, the tool including a target.

8. The medical system of claim 7, wherein the first monitored sensor data is received from the tool recognition assembly as the target is moved relative to the tool recognition assembly.

9. The medical system of claim 7, wherein the machine-readable instructions, when executed by the processor, further cause the control system to:
determine whether the target is recognized based on a comparison of the first baseline sensor value to the first monitored sensor data.

10. The medical system of claim 7, wherein determining if the tool is installed in the tool recognition assembly using the second baseline sensor value includes determining whether the tool is fully installed.

11. The medical system of claim 1, wherein the tool recognition assembly includes an inductance sensor.

12. The medical system of claim 11, wherein the first monitored sensor data includes instantaneous inductance data and the first baseline sensor value includes a baseline inductance value and wherein comparing the first monitored sensor data to the baseline adjustment threshold includes computing a ratio of the instantaneous inductance data to the baseline inductance value.

13. The medical system of claim 1, wherein the tool recognition assembly includes a proximal sensor and a distal sensor and wherein the proximal sensor generates a first proximal baseline sensor value that is the first baseline sensor value and the distal sensor generates a first distal baseline sensor value.

14. The medical system of claim 13, wherein the machine-readable instructions, when executed by the processor, further cause the control system to:
determine a first distal baseline adjustment threshold based on the first distal baseline sensor value;
receive second monitored sensor data from the tool recognition assembly;
compare the second monitored sensor data to the first distal baseline adjustment threshold for a second predetermined duration; and
if the comparison satisfies a second comparison criterion, establish a second distal baseline sensor value using the second monitored sensor data.

15. The medical system of claim 1, wherein the baseline adjustment threshold is determined based on an upper inductance ratio threshold chosen from a set of inductance ratio thresholds, and wherein each inductance ratio threshold in the set of inductance ratio thresholds is associated with one of a plurality of tools.

16. A method, comprising:
receiving a first baseline sensor value from a tool recognition assembly of a medical system subsequent to a set-up process of the tool recognition assembly and a receiving member, the receiving member configured to receive a tool;
determining a baseline adjustment threshold based on the first baseline sensor value;
receiving first monitored sensor data from the tool recognition assembly as the tool is inserted into the receiving member;
comparing the first monitored sensor data to the baseline adjustment threshold for a predetermined duration;
if the comparison satisfies a comparison criterion for the predetermined duration, establishing a second baseline sensor value using the first monitored sensor data; and
determining if the tool is fully inserted within the receiving member using the second baseline sensor value.

17. The method of claim 16, wherein the comparison criterion is the first monitored sensor data is lower than the baseline adjustment threshold for the predetermined duration and wherein the second baseline sensor value is lower than the first baseline sensor value.

18. The method of claim 16, wherein the comparison criterion is the first monitored sensor data is greater than the baseline adjustment threshold for the predetermined duration and wherein the second baseline sensor value is higher than the first baseline sensor value.

19. The method of claim 16, wherein the comparison criterion is that a ratio of first monitored sensor data to the baseline adjustment threshold is lower than 1 for the predetermined duration and wherein the second baseline sensor value is lower than the first baseline sensor value.

20. The medical system of claim 1, wherein the second baseline sensor value is established in response to retraction and reinsertion of the tool in the receiving member without removing the tool and reattaching the tool to the tool recognition assembly.

* * * * *